April 3, 1951 E. S. BOERNER Plant Pat. 1,010
ROSE PLANT
Filed Feb. 21, 1950
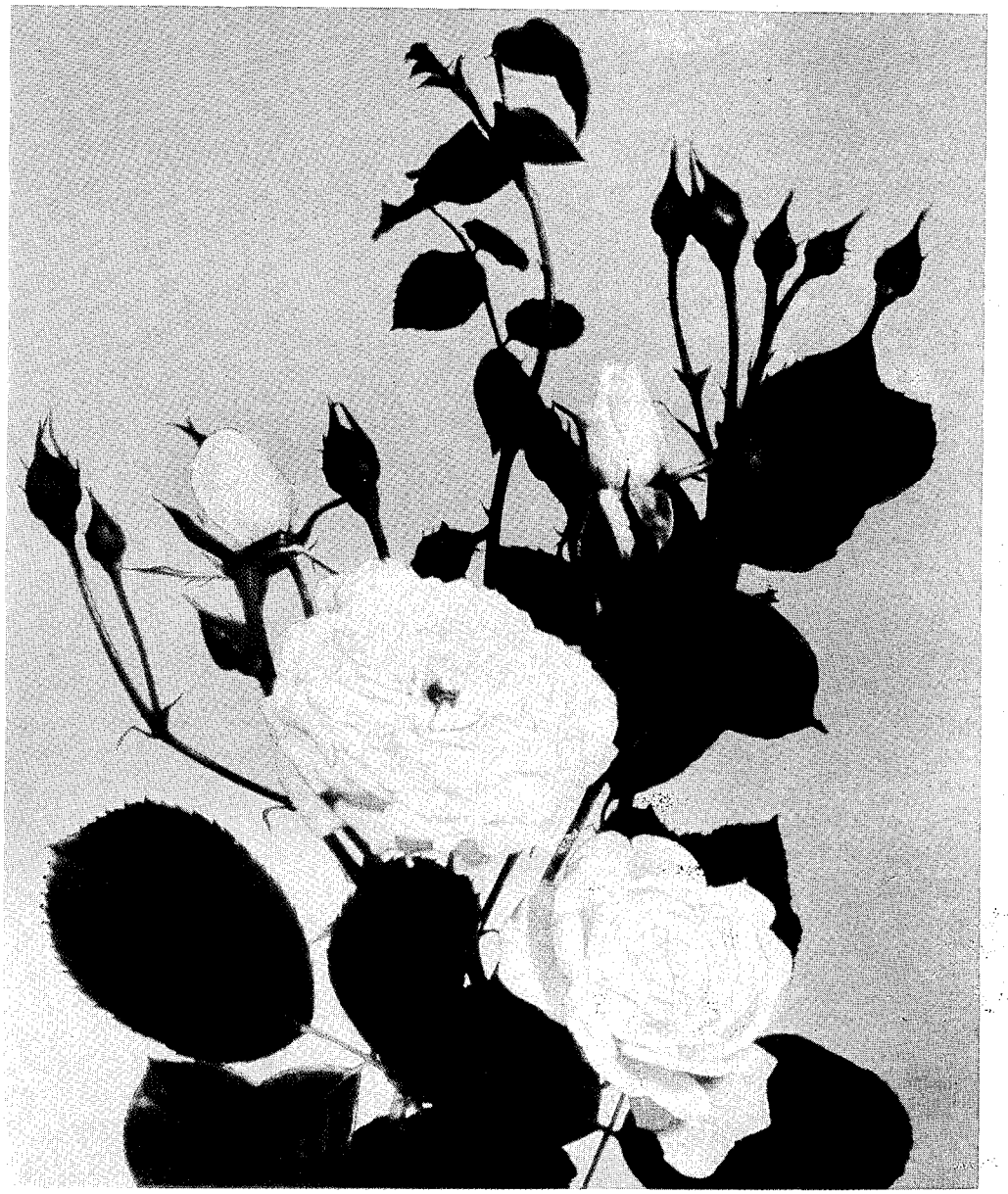
Inventor
E. S. Boerner,
By Robb & Robb
Attorneys Patented Apr. 3, 1951

Plant Pat. 1,010

UNITED STATES PATENT OFFICE 1,010

ROSE PLANT

Eugene S. Boerner, Newark, N. Y., assignor to Jackson & Perkins Company, Newark, N. Y., a corporation of New York Application February 21, 1950, Serial No. 145,357

1 Claim. (Cl. 47—61)

The present invention relates to a new and distinct variety of rose plant of the floribunda class, originated by crossing the variety "Mrs. R. M. Finch" (unpatented) with the well-known variety "Pinocchio" (Plant Patent No. 484).

The deliberate crossing of these two parent varieties had for its primary objective the blending of the semi-open plant habit of "Mrs. R. M. Finch" with the more compact close plant habit of "Pinocchio," and achieved the desired result by the fact that this new variety is more open than the parent "Pinocchio," and the plant habit more like "Mrs. R. M. Finch," while the flowers themselves are very similar to those of "Pinocchio" but are distinguished therefrom by their basically white color.

This combination of characteristics of the new variety is unique and exceedingly attractive in a rose plant of the large-flowered polyantha class.

Asexual reproduction of this new variety by budding at Newark, New York, and at Pleasanton, California, shows that the foregoing characteristics come true to form and are fixed and transmitted through succeeding propagations.

In the accompanying drawing are shown specimens of the new variety, with the flowers at different stages of development from small bud to full-open bloom.

The following is a detailed description of the new variety, with color terminology in accordance with Ridgway's Color Standards and Nomenclature:

Parentage: Seedling.
*Seed parent.*—"Mrs. R. M. Finch."
*Pollen parent.*—"Pinocchio."

Classification:
*Botanic.*—Large-flowered polyantha.
*Commercial.*—Floribunda.

*Flower*

Observations made in the field at Newark, New York, in the morning of September 8, 1949.

Blooming habit: Recurrent—continuous.

Bud:
*Size.*—Small.
*Form.*—Ovoid. Is not affected by wet or hot weather.
*Color.*—When sepals first divide—Pale Green Yellow, Plate 5. When petals begin to unfurl—Ivory Yellow, Plate 30. When half blown—inside of petals—Marguerite Yellow, Plate 30; reverse of petals—Sea-foam Yellow, Plate 31.
*Sepals.*—Serrated; branched. Curl back when petals begin to unfurl. Color—inside—Kildare green, Plate 31; outside—Light Bice Green, Plate 17.
*Calyx.*—Shape—pear. Size—small. Aspect—smooth. Odor when rubbed—none. Color—Scheele's Green, Plate 6.
*Peduncle.*—Length—short. Aspect—prickly. Color—Oil Green, Plate 5. Strength—erect; slender.
*Opening.*—Opens up well. Is not affected by adverse weather conditions.

Bloom:
Size.—Medium. Average size when fully expanded, 2½"–3".
*Borne.*—In flat clusters.
*Stems.*—Medium length; strong.
*Form.*—When first open—globular. Permanence—outer petals curl back.
*Petalage.*—Very double (many petals and stamens hidden). Number of petals under normal conditions, 50.
*Color.*—Center of flower—Maize Yellow, Plate 4. Outer petals—white, Plate 53. Base of petals (aiglet)—Citron Yellow, Plate 16. Inside of petals—white, Plate 53, lightly overcast with Marguerite Yellow, Plate 30. Reverse of petals—white, Plate 53, lightly overcast with Sea-foam Yellow, Plate 31. General tonality for a distance—Marguerite Yellow, Plate 30.
*Discoloration.*—General tonality at end of first day—Marguerite Yellow, Plate 30. Second day—white lightly overcast with Marguerite Yellow, Plate 30. Third day—white lightly overcast with Marguerite Yellow, Plate 30.

Petals:
*Texture.*—Thin. Is not affected by wet or hot weather.
*Appearance.*—Inside—shiny; outside—satiny.
*Form.*—Oval.
*Arrangement.*—Imbricated (regularly arranged shinglelike). Petaloids in center—few; small.
*Persistence.*—Drop off cleanly.
*Fragrance.*—Slight. Nature—fruity (Russet apple).
*Lasting quality.*—On the plant and as cut flower—long.

Genital organs:
*Stamens, anthers.*—Medium size; many. Color—Apricot Yellow, Plate 4. Arrangement—regular around styles.

*Stamens, filaments* (threads). — Medium lengths. Color—Empire Yellow, Plate 4.
*Pollen.*—Color—Maize Yellow, Plate 4.
*Styles.*—Loosely separated, uneven length; medium length; thin.
*Stigmas.*—Color—Amber Yellow, Plate 16.
*Ovaries.*—All enclosed in calyx.

*Plant*

Form: Bush.
Growth: Vigorous; compact.
Foliage: 5–7 leaflets.
*Size.*—Large.
*Quantity.*—Abundant.
*Color.*—New foliage: upper side—Oil Green, Plate 5; serrations—Oxblood Red, Plate 1; under side—Oil Yellow, Plate 5, overcast with Oxblood Red, Plate 1. Old foliage: upper side—Varley's Green, Plate 18; under side—Cress Green, Plate 31.
*Shape.*—Oval.
*Texture.*—Upper side—glossy; under side—smooth. Ribs and veins—prominent.
*Edge.*—Serrated (saw toothed).
*Serration.*—Single; large.
*Leaf stem.*—Color—Absinthe Green, Plate 31. Under side—smooth.
*Stipules.*—Long; serrated.

*Disease resistance.*—Resistant.
Wood:
*New wood.*—Color—Scheele's Green, Plate 6. Bark—smooth.
*Old wood.*—Color—Spinach Green, Plate 5. Bark—smooth.
Thorns:
*Thorns.*—Quantity—on main stalks from base—few; on laterals from stalk—few. Form — narrow base; medium length; hooked downward. Color when young—Yellowish Oil Green, Plate 5, with base Oxblood Red, Plate 1. Position—irregular.
*Prickles and short needles.*—None.

I claim:

A new and distinct variety of floribunda rose plant, characterized as to novelty by the combination of qualities of its parents, as evidenced by its more open plant habit like "Mrs. R. M. Finch," and by the similarity of its flowers to "Pinocchio" (Plant Patent No. 484), and by the basically white color of the flowers, substantially as shown and described.

EUGENE S. BOERNER.

No references cited.